US012635909B2

(12) United States Patent
Yin et al.

(10) Patent No.: US 12,635,909 B2
(45) Date of Patent: May 26, 2026

(54) METHOD AND APPARATUS FOR PROCESSING A CYCLIC PHYSIOLOGICAL SIGNAL

(71) Applicant: KONINKLIJKE PHILIPS N.V., Eindhoven (NL)

(72) Inventors: Bin Yin, Shanghai (CN); Haris Duric, Bothell, WA (US); Geert Guy Georges Morren, Vissenaken (BE); Steven Antonie Willem Fokkenrood, 's-Hertogenbosch (NL); Jens Muehlsteff, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/625,619

(22) Filed: Apr. 3, 2024

(65) Prior Publication Data

US 2024/0268712 A1      Aug. 15, 2024

Related U.S. Application Data

(63) Continuation of application No. 16/866,224, filed on May 4, 2020, now abandoned, which is a continuation (Continued)

(30) Foreign Application Priority Data

Feb. 12, 2010      (EP) ..................................... 10153489

(51) Int. Cl.
A61B 5/113          (2006.01)
A61B 5/00          (2006.01)
(Continued)

(52) U.S. Cl.
CPC ............ *A61B 5/113* (2013.01); *A61B 5/0205* (2013.01); *A61B 5/024* (2013.01); *A61B 5/0255* (2013.01);
(Continued)

(58) Field of Classification Search
None
See application file for complete search history.

(56) References Cited

U.S. PATENT DOCUMENTS 5,014,714 A      5/1991   Millay
5,311,876 A      5/1994   Olsen
(Continued)

FOREIGN PATENT DOCUMENTS

CN          101589952 A      12/2009
WO          2008096307 A1      8/2008

OTHER PUBLICATIONS

Jin, A., et al: "Performance Evaluation of a Tri-Axial Accelerometry-Based Respiration Monitoring for Ambient Assisted Living", 2009, IEEE Conf. On Eng. in Medicine & Biology, pp. 5677-5680.
(Continued)

*Primary Examiner* — Jacqueline Cheng
*Assistant Examiner* — Jairo H Portillo
(74) *Attorney, Agent, or Firm* — Leydig, Voit & Mayer, Ltd.

(57) ABSTRACT

The invention relates to a method and apparatus for processing a cyclic physiological signal (30, 40, 52, 53, 54). The method comprises the steps of repeatedly collecting (2) the physiological signal (30, 40, 52, 53, 54) over a time period (31, 32, 33) covering two or more cycles of the cyclic physiological signal (30, 40, 52, 53, 54), wherein a next time period (31, 32, 33) is adjacent to or overlaps with a previous time period (31, 32, 33), extracting values (3, 13) of a set of predefined parameters from the physiological signal (30, 40,
(Continued)

52, 53, 54) within each time period (31, 32, 33) which parameter values characterize the physiological signal (30, 40, 52, 53, 54) within the time period (31, 32, 33), and classifying (4, 14) the physiological signal (30, 40, 52, 53, 54) within each time period (31, 32, 33) based upon the extracted set of predefined parameter values. This provides for an efficient analysis of a cyclic physiological signal which is especially suitable for continuous monitoring of patients where a trend of a reliable physiological signal is more important than an instantaneous measurement of a reliable physiological signal, such as in a general ward environment of a hospital and/or in a home environment.

18 Claims, 6 Drawing Sheets

Related U.S. Application Data of application No. 13/576,687, filed as application No. PCT/IB2011/050510 on Feb. 7, 2011, now abandoned.

(51) Int. Cl.

| | | |
|---|---|---|
| *A61B 5/0205* | (2006.01) | |
| *A61B 5/024* | (2006.01) | |
| *A61B 5/0255* | (2006.01) | |
| *A61B 5/08* | (2006.01) | |

(52) U.S. Cl.
CPC .......... *A61B 5/0816* (2013.01); *A61B 5/7221* (2013.01); *A61B 5/7264* (2013.01); *A61B 5/721* (2013.01); *A61B 5/7275* (2013.01); *A61B 2562/0219* (2013.01)

(56) References Cited

U.S. PATENT DOCUMENTS

| | | | |
|---|---|---|---|
| 5,339,818 | A | 8/1994 | Baker |
| 5,546,952 | A | 8/1996 | Erickson |
| 5,931,858 | A | 8/1999 | Kadhiresan |
| 6,997,882 | B1 | 2/2006 | Parker |
| 7,160,252 | B2 | 1/2007 | Cho |
| 7,559,903 | B2 | 7/2009 | Moussavi |
| 8,094,013 | B1 | 1/2012 | Lee |
| 2002/0013533 | A1 | 1/2002 | Oka |
| 2002/0183644 | A1 | 12/2002 | Levendowski |
| 2003/0187364 | A1 | 10/2003 | Hamilton |
| 2004/0111038 | A1 | 6/2004 | Salla |
| 2004/0186388 | A1 | 9/2004 | Gerasimov |
| 2004/0249314 | A1 | 12/2004 | Salla |
| 2005/0027216 | A1 | 2/2005 | Gullemaud |
| 2005/0121477 | A1 | 6/2005 | Meyer |
| 2005/0121478 | A1 | 6/2005 | Kim |
| 2005/0187483 | A1 | 8/2005 | Kolluri |
| 2006/0178591 | A1 | 8/2006 | Hempfling |
| 2007/0118054 | A1 | 5/2007 | Pinhas |
| 2008/0161654 | A1 | 7/2008 | Teller et al. |
| 2008/0161707 | A1 | 7/2008 | Farrington |
| 2008/0269625 | A1 | 10/2008 | Halperin |
| 2008/0275349 | A1 | 11/2008 | Halperin |
| 2009/0062628 | A1 | 3/2009 | Yamamoto |
| 2009/0118626 | A1 | 5/2009 | Moon |
| 2009/0143694 | A1 | 6/2009 | Krauss et al. |
| 2009/0241954 | A1 | 10/2009 | Karlsson |
| 2010/0298730 | A1* | 11/2010 | Tarassenko .......... A61B 5/0816 703/2 |
| 2011/0066062 | A1* | 3/2011 | Banet .................... A61B 5/113 600/534 |

OTHER PUBLICATIONS

Reinvuo, T. et al: "Measurement of Respiratory Rate With High-Resolutin Accelerometer Adn Emfit Pressure Sensor", 2006, IEEE Sensors Appl. Sysmposium pp. 192-195.

* cited by examiner

METHOD AND APPARATUS FOR PROCESSING A CYCLIC PHYSIOLOGICAL SIGNAL

CROSS-REFERENCE TO PRIOR APPLICATIONS

This application is a Continuation Application of U.S. Ser. No. 16/866,224 filed May 4, 2020 which is a Continuation of National Phase application under 35 U.S.C. § 371, Ser. No. 13/576,687, filed on Aug. 2, 2012, which claims the benefit of International Application Serial No. PCT/IB2011/050510, filed on Feb. 7, 2011, which claims the benefit of European Application No. 10153489.9, filed on Feb. 12, 2010. These applications are hereby incorporated by reference herein.

FIELD OF THE INVENTION

The invention relates to a method and apparatus for processing a cyclic physiological signal.

BACKGROUND OF THE INVENTION

The monitoring of vital body signs of patients, such as respiration rate and heart rate, in an intensive care environment in a hospital has requirements different from those in monitoring a patient in a general ward setting or in a home environment. The intensive care unit of a hospital requires an instantaneous and high reliability of the monitored parameters, whereas the general ward environment of a hospital is more focused on the trend of the monitored parameters.

As an example, respiration rate has proven to be a good indicator of the deterioration of the condition of a patient and it plays a crucial role in early warning hospital systems in combination with other vital body signs. Therefore, a need for continuous and reliable monitoring of a respiration signal is seen especially in the intensive care units of hospitals. A similar need, with less stringent requirements on the reliability and the instantaneous presentation of the monitored parameters, is present in the general ward settings of hospitals and in home healthcare applications, such as in telemedicine and chronic disease management. While continuous monitoring of the respiration signal, from which the respiration rate is extracted, is available on bedside monitors for intensive care patients, various portable sensor systems are being developed to allow unobtrusive and prolonged measurement and monitoring of the respiration signal of mobile patients in general wards with minimal discomfort.

Motion artifact is a well known issue in patient monitoring as a whole, which refers to a contamination of the physiological signal and a degradation of the measurement quality caused by physical activities of a patient, such as posture change, movement and talking. Especially for cyclic physiological signals it can become very difficult to extract the right frequency from the contaminated cyclic signal. The motion artifact issue is more pronounced in a general ward setting than in an intensive care unit setting, since patients in the general ward setting generally have a more mobile activity pattern and are monitored most of the time without constant nursing surveillance, thus lacking knowledge on the presence of physical activities and the measurement context. The problem becomes even more severe in the monitoring of patients in home healthcare settings.

To allow the reliable use of such continuous monitoring systems, the issue of motion artifacts must be tackled. Most of the reported studies focus on various signal retrieval schemes, where often adaptive noise cancellation is applied for cleaning up the motion-contaminated signal. There are a couple of intrinsic difficulties in these schemes that are hard to overcome. For example, motion artifacts may be induced by multiple noise sources that are difficult to identify and estimate. Another drawback is that these schemes usually require a large computational effort and are thus not efficient for a portable system.

U.S. Pat. No. 5,546,952 discloses a method and device for determining the validity of a respiratory waveform from a signal having non-respiratory artifacts, including monitoring a respiratory effort waveform for a parameter of the waveform that is characteristic of a non-respiratory artifact. The parameter is compared with a predetermined limit to determine whether a valid respiratory waveform has been detected. This is useful in obstructive sleep apnea treatment where, in case a valid respiratory effort waveform is available, electrical stimulation of a patient is then validly limited to the inspiratory phase of the respiratory cycle, and, in case a valid respiratory effort is not detected, electrical stimulation is suppressed. The selected parameters of the waveform that are monitored can be, for example, inspiratory rise time, inspiratory time-to-peak, time of inspiratory onset to expiratory offset, inspiratory peak-to-peak time, expiratory peak-to-peak time or breath-to-breath time. Initialization of the respiratory signal analysis process occurs when the system is turned on or reset in which the system tracks several respiratory cycles to set an amplifier gain and to establish the normal morphological parameters of the waveform. A time reference is established with respect to the last inspiratory onset so that a predicted onset can be calculated for the next breath which is used to synchronize the electrical stimulation with the respiratory cycle in case of a valid respiratory effort waveform. Although this method does not apply adaptive noise cancellation, it still is aimed at providing a reliable instantaneous respiration signal on a peak-by-peak basis, which is important in intensive care settings, but which is not a prerequisite in a general ward setting.

SUMMARY OF THE INVENTION

It is an object of the present invention to provide an efficient analysis of a cyclic physiological signal which is especially suitable for continuous monitoring of patients where a trend of a reliable physiological signal is more important than an instantaneous measurement of a reliable physiological signal on a peak-by-peak basis, such as in a general ward environment of a hospital and/or in a home environment.

In a first aspect of the present invention a method of processing a cyclic physiological signal is provided, the method comprising the steps of:

repeatedly collecting the physiological signal over a time period covering a two or more cycles of the cyclic physiological signal, wherein a next time period is adjacent to or overlaps with a previous time period;

extracting values for a set of predefined parameters from the physiological signal within each time period which parameters characterize the physiological signal within the time period; and classifying the physiological signal within each time period based upon the extracted set of predefined parameter values.

The method according to the invention thus provides a classification of different time periods or frames of a cyclic physiological signal based on a set of characteristic parameters or features the values of which are extracted only for that specific time period or segment of the physiological signal. There is no instantaneous signal analysis, such as for example on a peak-by peak basis, but rather a time frame, or time segment, of the periodic, or cyclic, physiological signal is analyzed, wherein the time segment spans two or more cycles. By repeating the analysis of the physiological signal for each of the different time periods, the total physiological signal will be segmented or divided up into several time periods each being classified separately. Thus, each selected time period or segment of the physiological signal is characterized by a specific classification, which can be used, for example, for indicating to what extent the physiological signal is contaminated by, for example, motion artifacts. So, instead of retrieving information out of contaminated measurement results, a signal analysis is employed which automatically identifies and classifies signal segments, for example as a quality measure which indicates how well each signal segment represents the physiological measurement. The signal analysis runs in a sliding time window mode. The time window or time period, covering at least a couple of cycles, slides over the signal trace and the signal segment within each time window or period is analyzed by extracting values for the set of predefined parameters and by classifying the signal segment within each time window based on these extracted parameter values. The method provides for an improved way of trending a physiological signal resulting in a reliable and classified physiological signal thus providing a replacement of the computationally intensive instantaneous representation of an artifact-free physiological signal.

In an embodiment of the method according to the invention, the method further includes a step of extracting the frequency of the classified physiological signal for each time period, after the step of classifying the physiological signal. The calculation of the frequency or rate of the cyclic physiological signal is performed based on the classified physiological signal, thus ensuring a reliable input for the extraction of frequency of the physiological signal. The frequency of the physiological signal for example comprises a respiration rate or a heart rate, which can be defined as the number of breaths per minute or the number of heart beats per minutes, respectively.

In a further embodiment, the method further includes a step of calculating a confidence value for the extracted frequency of the physiological signal within each time period after the step of extracting the frequency and based upon the values of the set of predefined parameters extracted from the physiological signal in the corresponding time period and the extracted frequency value. In certain circumstances, not only the frequency of the physiological signal but also knowledge about the confidence of the calculated frequency is important. This information provides useful input in further processing of the frequency data, for example for the proper selection of a frequency or rate to report and appropriate frequency or rate trend analysis.

In an embodiment of the method according to the invention, the step of classifying comprises labeling each time period as accept or as reject. In this way it is decided for each time period of the physiological signal whether the physiological signal in that time period is acceptable, or in other words resembles a normal physiological signal without any significant contamination, or whether the physiological signal in that time period is not acceptable, for example as a result of motion artifacts. This provides for a processed physiological signal with time periods that are classified as not acceptable or bad, which time periods then may be ignored in the further processing of the physiological signal. On the other hand, the time periods of the processed physiological signal that are classified as acceptable or good, can be considered to be a reliable representation of the physiological signal without any significant disturbance and thus can be used as a reliable input for further processing of the signal.

In a preferred embodiment, the frequency of the physiological signal is not extracted for each time period that is labeled as reject. In this way it is prevented that a time period which contains a contaminated physiological signal is used to calculate an erroneous frequency of the cyclic physiological signal. Only the signal segments identified as good or acceptable will be further processed, so that the extraction of the frequency generates meaningful values of the frequency.

In an embodiment of the method according to the invention, the physiological signal represents a respiration and/or pulse of a patient. The respiration and the pulse represent the most important physiological signals. The frequency of the signal is then represented as the respiration rate and/or the pulse rate.

In an embodiment of the method according to the invention, the predefined parameters characterize the physiological signal as a function of time, frequency and/or position in space. Parameters as a function of time can be, for example, signal variance, peak-to-peak value and temporal correlation. Parameters as a function of frequency can be, for example, dominant frequency and spectral entropy. Parameters as a function of position in space can be, for example, correlation between axes representing the position in the Cartesian coordinate system in case a multi-axis accelerometer is used as a physiological signal sensing device, where a respiration movement usually takes place in one plane of the sensor and thus signals from the two axes in this plane have a strong correlation whereas the axis perpendicular to this plane mainly measures noise, which will help distinguishing a good physiological measurement from one contaminated by motion.

In an embodiment of the method according to the invention, the step of classifying is performed only for the part of the next time period that does not overlap with the previous time period in the case of an overlap between the next and previous time period. By applying an overlap of two consecutive time periods, an improved resolution in time is achieved and the reliability and robustness of the classification is improved. For example, in case of an overlap of 50% of two consecutive time periods, half of the data in the current time period is from the previous time period that is already analyzed and classified in a previous step, and half of the data in the current time period is new and not yet analyzed. The classifying step uses the parameter values derived for the entire current time period but only classifies or labels the new part of the time period, for example as good or bad. The amount of overlap between consecutive time periods can be optimized for a good trade-off of the classification resolution in time and motion artifacts propagation over consecutive time periods.

In an embodiment of the method according to the invention, the step of classifying is also based upon a statistical database of the set of predefined parameters. The increased set of input data used for the classification step provides for an improved reliability of the classification of the physiological signal.

In an embodiment of the method according to the invention, the method further includes a step of conditioning the physiological signal before the step of repeatedly collecting the physiological signal, wherein the step of repeatedly collecting the physiological signal comprises repeatedly collecting the conditioned signal. For example, the signal conditioning comprises a filtering of the physiological signal such that frequencies corresponding to frequencies that are representative for the cyclic physiological signal pass the filtering step. This reduces noise and possible further unwanted environmental influences on the physiological signal. For example, if the physiological signal should be indicative of respiration, the conditioning step preferentially filters the physiological signal such that frequencies corresponding to possible frequencies of the respiration motion pass the filtering step. In this case, frequencies within a frequency range between 0 Hz and 2 Hz preferentially pass the filtering step. As another example, if the physiological signal is indicative of the heart activity of a person, the filtering step preferentially filters the accelerometer signals such that frequencies corresponding to possible frequencies of heart activity motion pass the filtering unit, for example in case an acceleration sensor is used, the conditioning step can be adapted to filter the physiological signals such that frequencies within the frequency range of between 5 Hz and 20 Hz pass the filtering step, since in this frequency range the mechanical vibrations caused by the beating heart, which corresponds to a heart rate occurring in a range between approximately 0.5 Hz to 4 Hz or approximately 30 to 240 beats per minute, are captured by the accelerometer. After taking the envelope of the filtered signal, a bandpass filter between 0.5 Hz and 4 Hz is applied for generating a signal for the heart rate calculation. A combination of respiration and heart activity filtering could also be implemented. By conditioning the signal before it is analyzed, for example by noise filtering and/or signal normalization, gross contaminations are filtered which results in an improved and more reliable and robust signal analysis.

In an embodiment of the method according to the invention, multiple physiological signals are collected simultaneously and the steps of extracting and classifying are performed for each of the multiple physiological signals separately. For example, physiological signals measured at different locations of a body of a patient may react to motion artifacts differently, thereby creating complementary classified physiological signals within corresponding time periods, which leads to an increased availability of useful physiological signals in time as well as a more robust and reliable classification.

In a second aspect of the present invention an apparatus for monitoring a cyclic physiological signal is provided, the apparatus comprising:

> a sensor adapted for measuring the cyclic physiological signal;

> a time period definition unit adapted for repeatedly defining a time period covering two or more cycles of the cyclic physiological signal, in which time period the physiological signal is analyzed, wherein a next time period is adjacent to or overlaps with a previous time period;

> an extraction unit adapted for extracting values for a set of predefined parameters from the physiological signal within the time period which parameters characterize the physiological signal within the time period; and > a classifying unit adapted for classifying the physiological signal within the time period based upon the extracted set of predefined parameter values.

In an embodiment of the apparatus according to the invention, the sensor comprises a multi-axial accelerometer and the measured physiological signal comprises multiple sub-signals corresponding to the multiple axes and which sub-signals are analyzed synchronously in time. A multi-axial accelerometer is a device that measures the acceleration in multiple sensing axes, and may for example be used as an inclinometer to reflect the abdomen or chest movement caused by respiration or to measure the mechanical vibration of the body surface reflecting the heart activity. The multi-axial accelerometer is, for example, a tri-axial accelerometer being adapted to generate three accelerometer signals indicative of the acceleration along three orthogonal spatial axes, wherein the time period definition unit is adapted to combine these three accelerometer signals for analyzing the combined signal. It is preferred that the multi-axial accelerometer is adapted to be positioned at a body part of a person, wherein the measured signal is a motion signal indicative of at least one of respiration and heart activity of a person. For generating a motion signal indicative of respiration the multi-axial accelerometer is preferentially positioned at the costal arch, roughly half way between the central and lateral position. However, the multi-axial accelerometer can also be located at other positions, for example, on the abdomen, in particular, if limitations due to body physique like post-surgery wounds apply. For generating a motion signal indicative of heart rate the multi-axial accelerometer is preferentially positioned on the left side of the abdomen/thorax. It is further preferred that the accelerometer is positioned at the costal arch, in particular, at the cartilage of the left lower ribs. A further preferred position of the multi-axial accelerometer for generating a motion signal indicative of heart rate is a higher position on the thorax or a lower position on the abdomen. In particular, the preferred positions for determining a motion signal indicative of respiration are also preferred for measuring a motion signal indicative of heart rate. Especially, for generating a motion signal indicative of respiration and heart rate the multi-axial accelerometer is preferentially positioned at the costal arch, half way central-lateral on the left side.

In an embodiment of the apparatus according to the invention, the apparatus further comprises a frequency determination unit for determining the value of the frequency of the classified physiological signal. In a preferred embodiment the apparatus comprises multiple sensors and is suitable for measuring multiple physiological signals each of which is analyzed either separately or in combination.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF EMBODIMENTS

Figure 1:
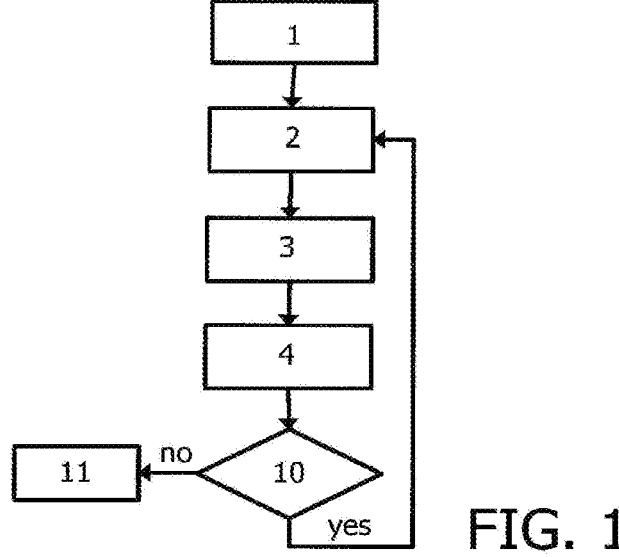
FIG. 1 shows a flowchart exemplarily illustrating an embodiment of a method of processing a cyclic physiological signal.

FIG. 1 shows a flowchart exemplarily illustrating an embodiment of a method of processing a cyclic physiological signal. In step 1 a cyclic physiological signal is captured, in this embodiment with a sensor located on a suitable location of an object, in this example a person. The person may be a patient in an intensive care department of a hospital, but also a patient in a general ward department of a hospital, in which the patient is more mobile and is monitored less severe than in the intensive care environment. Furthermore, the person could be located in his own home environment. The sensor may, for example, comprise a multi-axial accelerometer which is adapted to generate accelerometer signals indicative of the acceleration along different spatial axes. In this embodiment, the multi-axial accelerometer is a tri-axial accelerometer being adapted to generate three accelerometer signals indicative of the acceleration along three orthogonal spatial axes. For example, tri-axial accelerometers named ST Microelectronics LIS344ALH or Kionix KXM52 can be used. However, also other kinds of multi-axial accelerometers can be used for generating accelerometer signals indicative of the acceleration along different spatial axes. The cyclic physiological signal may be the respiration or the heart beat of the person. Respiration rate is one of the most important vital body signs in patient monitoring and it has proven to be a good indicator of the deterioration of patient conditions, and it plays a crucial role in early warning hospital systems in combination with other vital body signs, such as the heart rate.

In step 2 of FIG. 1 a time period is defined and the physiological signal is collected over that time period. The time period covers two or more cycles of the physiological signal, preferably at least five cycles. The time period is typically a few to a few tens of seconds depending on the type of physiological signal that is monitored. For example, the time period for respiration signal classification may be chosen from 30 seconds up to one minute, in which about 5 to 30 breaths may be covered, which is a typical frequency range of respiration.

In step 3 of FIG. 1 values are extracted for a set of predefined parameters from the signal segment within the time period that was defined in step 2. The parameters and their values characterize the signal segment within the current time period in various aspects such as in time, in frequency and in spatial coordinates, i.e. the position in space. To grasp distinct features of, for example, a respiration or heart beat signal, specific characteristics of the signal can be defined. Characteristic parameters as a function of time are, for example, signal variance, peak-to-peak value and temporal correlation. Characteristic parameters as a function of frequency are, for example, dominant frequency and spectral entropy. A characteristic parameter as a function of spatial coordinates is, for example, the correlation between the three orthogonal spatial axes as measured with a three-axial accelerometer. A typical respiration signal measured by an accelerometer is of low signal variance, periodic with a frequency ranging from 0.05 Hz to 2 Hz and has strong inter-axis correlation. The extracted parameter values map each signal segment to a point in the parameters space.

In step 4 of FIG. 1 the signal segment within time period defined in step 2 is classified based on the set of predefined parameter values that were extracted in step 3. The classification may be a straightforward good-bad classification of the signal segment within the current time period, indicating whether the signal in the current time period resembles, for example, a respiration signal or not. The classification may also result in an indication as to what extent the physiological signal is contaminated by, for example, motion artifacts.

In step 10 of FIG. 1 it is checked if a next time period should be defined. If no next time period has to be defined, for example because the end of the signal is reached, then the method stops in step 11. If a next time period can be and/or should be defined, then the method returns to step 2 and a next time period is defined. The next time period may be adjacent to the previous time period. Alternatively, the next time period overlaps the previous time period. By applying an overlap of two consecutive time periods, an improved resolution in time is achieved. After the definition of the next time period, the method continues with step 3 in which a set of predefined parameter values is extracted for the signal segment that is within this next time period, followed by step 4 in which the signal segment located within this next time period is classified based on the set of predefined parameter values that were extracted in the previous step. In case this next time period overlaps the previous time period, for example, in case of an overlap of 50% of two consecutive time periods, half of the data in the current time period is from the previous time period that is already analyzed and classified in the previous step, and only half of the data in the current time period is new and not analyzed. In this case the classifying step uses the parameter values derived for the entire current time period but only classifies or labels the new part of the time period, for example as good or bad.

Figure 2:
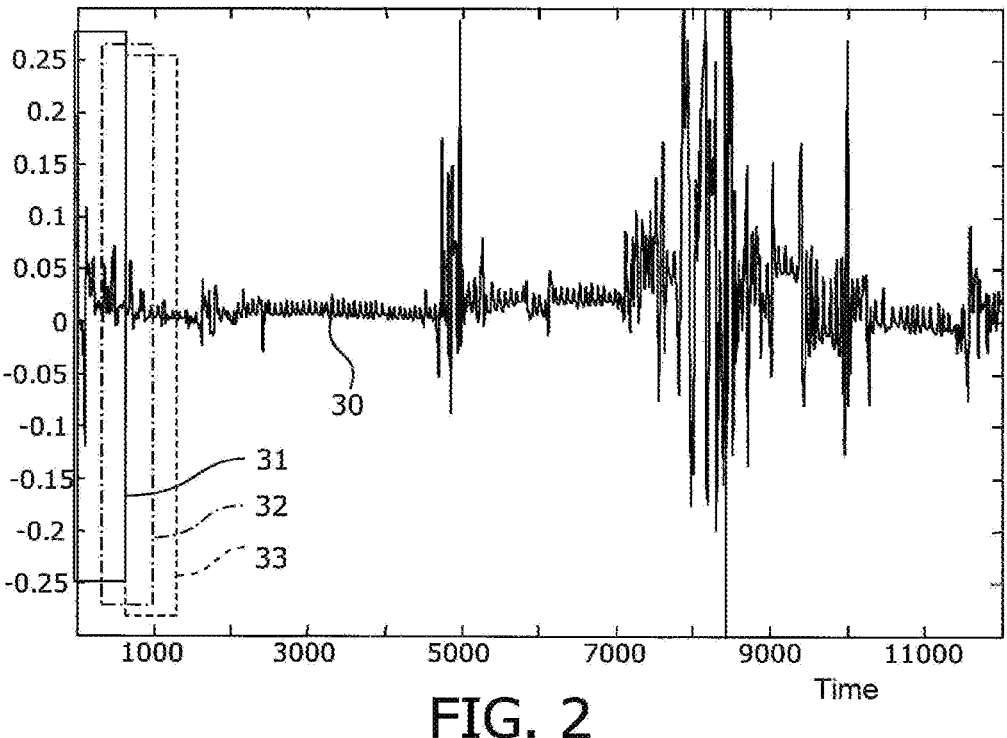
FIG. 2 shows schematically and exemplarily an example of defining the time periods for segmented signal analysis.

FIG. 2 shows schematically and exemplarily an example of a respiration signal 30 as a function of time in which time periods 31, 32, 33 are defined for a segmented signal analysis. The horizontal axis of the graph in FIG. 2 represents time in arbitrary units and the vertical axis represents the amplitude of the respiration signal in arbitrary units. FIG. 2 illustrates that this embodiment applies time periods that overlap consecutively. The first time period 31 overlaps with the second time period 32 and the second time period 32 overlaps with the third time period 33. The other time periods, following after time period 33, are not shown in the graph. According to the method illustrated by the flowchart of FIG. 1, in step 2 the first time period 31 is defined first. The part of the respiration signal 30 that is within the first time period 31 is analyzed in steps 3 and 4 of FIG. 1 comprising first an extraction of the values for a first set of predefined parameters and then a classification of the part of the signal 30 that is within the first time period 31. In the next loop the second time period 32 is defined and the data of the part of the signal 30 that are within the second time period 32 are collected and used for extracting the values of a second set of predefined parameters for the signal segment within this second time period 32. Because the part of the first time period 31 that overlaps with the second time period 32 is already classified in the previous classification step, in this embodiment, only the part of the signal 30 is classified that is within the part of the second time period 32 that does not overlap with the first time period 31. Then the third time period 33 is defined and the data of the part of the signal 30 that is within the third time period 33 are collected and used for extracting the values of a third set of predefined parameters for the signal segment within this third time period 33. Because the part of the second time period 32 that overlaps with the third time period 33 is already classified in the previous classification step, in this embodiment, only the part of the signal 30 is classified that is within the part of the third time period 33 that does not overlap with the second time period 32. These steps are repeated until the whole signal 30 is covered with consecutive time periods (not shown). The amount of overlap between consecutive time periods can be optimized for a good trade-off of the classification resolution in time and motion artifacts propagation over consecutive time periods. The time periods, each classifying a time segment of the signal 30, slide over the signal 30 thereby providing a segmented signal analysis and classification.

Figure 3:
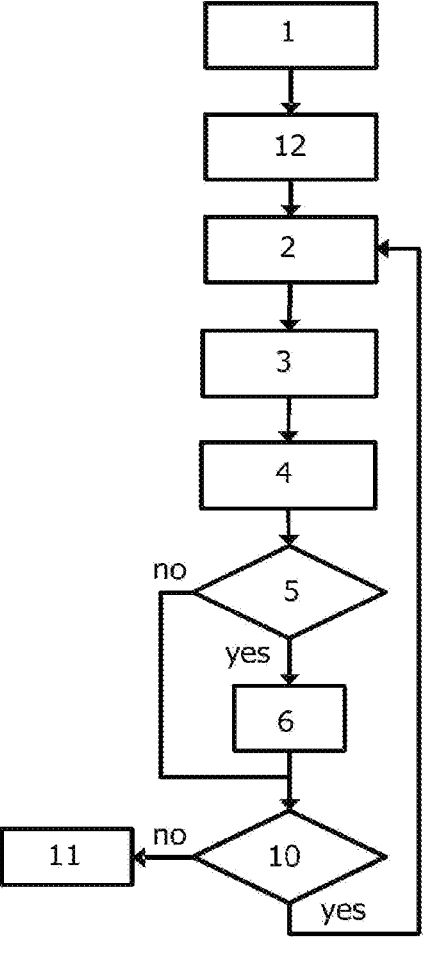
FIG. 3 shows a flowchart exemplarily illustrating another embodiment of a method of processing a cyclic physiological signal.

FIG. 3 shows a flowchart exemplarily illustrating another embodiment of a method of processing a cyclic physiological signal. The method illustrated in FIG. 3 is an extension of the method that is illustrated in FIG. 1. Steps 1, 2, 3, 4, 10 and 11 of FIG. 1 are the same steps in FIG. 3. In this embodiment, after step 1 a step 12 provides a conditioning of the signal captured in step 1. The conditioning of the signal may comprise, for example, a filtering of the signal to improve the signal quality before it is analyzed in the next steps of the method. For example, step 12 comprises filtering of the signal such that frequencies corresponding to possible frequencies of respiration or of heart activity are passed. In particular, the filtering step can be adapted to filter frequencies such that a typical heart rate or frequency range between 0.5 Hz and 4 Hz is passed. It should be noted that in a frequency range between approximately 5 Hz and 20 Hz the mechanical vibrations caused by the beating heart, which corresponds to a heart rate occurring in a range between approximately 0.5 Hz to 4 Hz or approximately 30 to 240 beats per minute, are captured by the accelerometer. After taking the envelope of the filtered signal, a bandpass filter, filtering the frequency range of the heart rate, is applied for generating a signal for the heart rate calculation. It is also possible that for determining respiration frequencies the signal is filtered in a frequency range between 0 Hz and 2 Hz and that for determining heart rate frequencies the signal is filtered such that only a frequency range between approximately 0.5 Hz and 4 Hz passes. A combination of these two frequency ranges or another frequency range may also be an option. In this embodiment in step 2 the conditioned physiological signal is collected over the selected time period.

In step 5 of FIG. 3 it is decided if the signal segment within the current time period is good or bad, i.e. to be accepted or to be rejected, based on the results of the classification of the signal segment in previous step 4. For example in case of a respiration signal, the signal segment within the current time period is classified as good or acceptable if it resembles a breathing signal, and it is classified as bad or is rejected if it does not resemble a breathing signal because of, for example, contamination by motion artifacts as a result of physical movement of the person. If the signal segment within the current time period is accepted in step 5, then in step 6 the frequency or rate of the cyclic signal is calculated for the part of the signal that is within the current time period. Because, the signal segment is classified as good and thus resembles the required physiological signal, the value of the frequency or rate calculated for this signal segment will be a reliable value. For example, in case of a respiration signal in step 6 the respiration rate is calculated and in case of a heart beat signal the pulse rate is calculated. The calculated respiration rate and/or pulse rate can be shown on a display (not shown). On the other hand, if the signal segment within the current time period is rejected in step 5, then no frequency or rate will be calculated for the signal segment within this time period. In this case the signal within the current time period does not resemble a required physiological signal, for example a breathing or heart beat signal, and a calculation of a respiration rate or a pulse rate for this signal segment will result in an inaccurate value. To enhance the visibility of rejected signal segments, the signal segment in this time period can be labeled as bad or rejected by overlaying a colored bar over the signal for this time period on a display showing the signal as a function of time.

Various classification algorithms may be used for the good/bad signal classification. Commonly used classifiers include rule-based, Bayesian, artificial neural network, decision tree, linear discriminant function and k nearest neighbor classifiers. The selection and design of such a respiration-specific classifier may include the use of a statistically complete respiration database of mobile subjects, with which a chosen classifier is trained and its classification performance is evaluated. Criteria, such as computational complexity and interpretability of the algorithm, can also be important in the selection of the classifier. The resultant classifier is usually a good trade-off of multiple criteria. Note that the generation of the good/bad classifier is completed offline, and the execution of classification is instant and computationally light, enabling a real-time physiological signal analysis.

Figure 4:
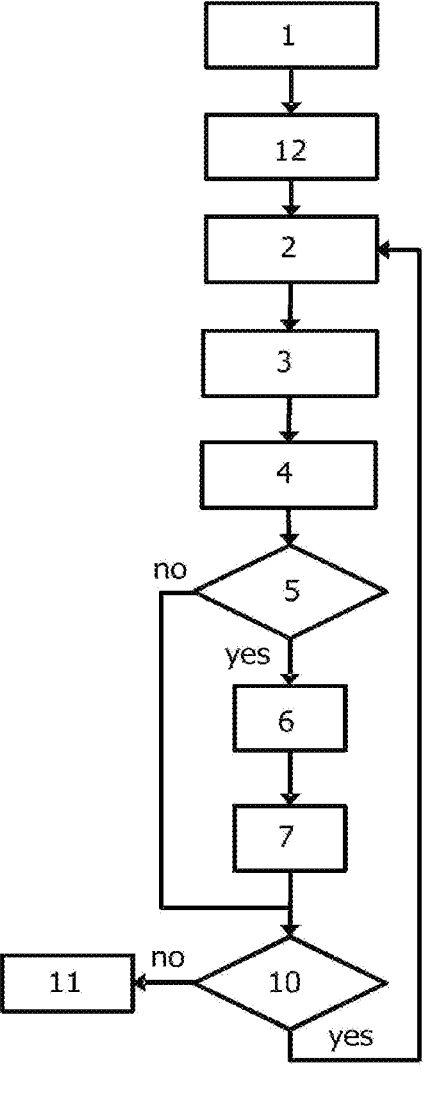
FIG. 4 shows a flowchart exemplarily illustrating another embodiment of a method of processing a cyclic physiological signal.

FIG. 4 shows a flowchart exemplarily illustrating another embodiment of a method of processing a cyclic physiological signal. The method illustrated in FIG. 4 is an extension of the method that was illustrated in FIG. 3. Similarly numbered steps of FIG. 3 are the same steps in FIG. 4. In this embodiment, after step 6 in a step 7 a confidence index of the calculated frequency is calculated for the part of the signal in the present time period if this signal segment is classified as acceptable. The confidence index indicates the confidence or the accuracy of the calculated frequency in step 6. The confidence index may be defined using the values of the parameters extracted in step 4 for the corresponding signal segment in combination with the calculated value of the frequency, for example the value of the respiration rate or heart rate. The confidence index provides useful input in further processing of the respiration rate or heart rate data, for example in proper reporting of the respiration rate and appropriate respiration rate trend analysis.

Figure 5:
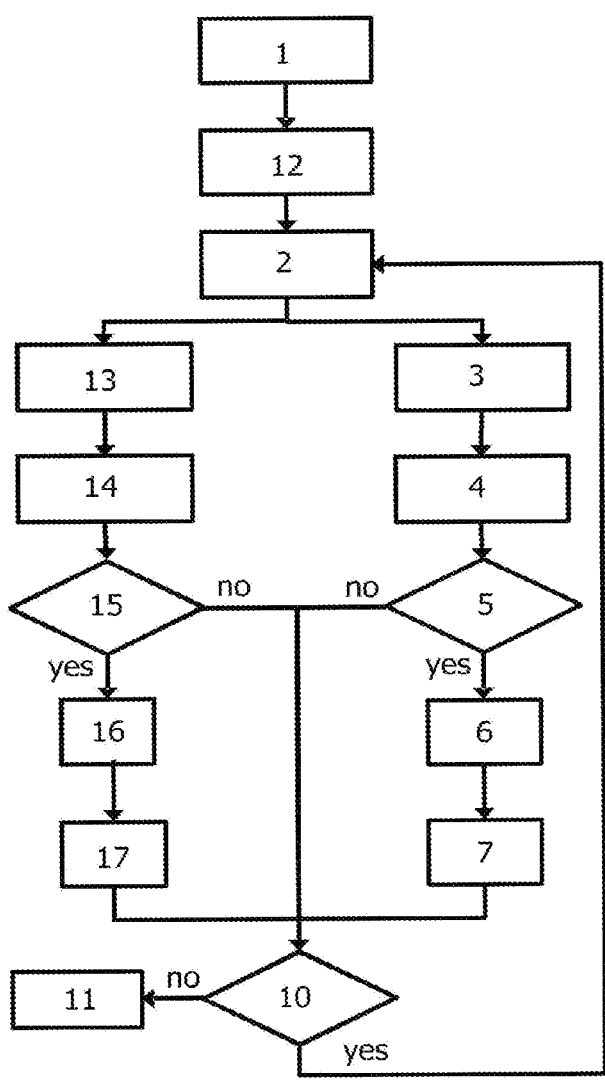
FIG. 5 shows a flowchart exemplarily illustrating another embodiment of a method of processing a cyclic physiological signal.

FIG. 5 shows a flowchart exemplarily illustrating another embodiment of a method of processing a cyclic physiological signal. The method illustrated in FIG. 5 is an extension of the method that was illustrated in FIG. 4. Similarly numbered steps of FIG. 4 are the same steps in FIG. 5. In FIG. 5 the signal is captured in step 1 with an accelerometer. When an accelerometer is used as a sensing device, not only respiration but also heart beat or pulse information can be measured. This is depicted in FIG. 5, where a branch dedicated to heart signal analysis is incorporated next to the already existing branch in which, in this embodiment, the respiration signal is analyzed, comprising steps 3, 4, 5, 6 and 7. Step 12 in this embodiment is adapted to filter the accelerometer signals with a filter for filtering both the accelerometer signals for determining respiration and the accelerometer signals for determining heart rate. Alternatively, two separate and dedicated filters may be applied, a first filter for filtering the accelerometer signals for determining respiration and a second filter for filtering the accelerometer signals for determining heart rate. Because heart beating causes mechanical vibration of the body surface that is measured as inertial acceleration by the sensor (and small inclination changes), the pulse signal is treated in a higher frequency band than for the respiration signal.

In step 13 of FIG. 5 values are extracted for a set of predefined parameters from the pulse signal segment within the time period that was defined in step 2. The parameters and their values characterize the pulse signal segment within the current time period in various aspects such as in time, in frequency and in spatial coordinates, i.e. the position in space. To grasp distinct features of the heart beat signal, specific characteristics of the signal can be defined. Characteristic parameters of the pulse signal as a function of time are, for example, signal variance, signal mean and correlation in time. Characteristic parameters as a function of frequency are, for example, dominant frequency and spectral entropy. A characteristic parameter as a function of spatial coordinates is, for example, the correlation between the three orthogonal spatial axes as measured with a three-axial accelerometer. A typical pulse signal measured by an accelerometer is periodic with a frequency ranging between 0.5 Hz and 4 Hz and has strong inter-axis correlation. It should be noted that in a frequency range between approximately 5 Hz and 20 Hz the mechanical vibrations caused by the beating heart, which corresponds to a heart rate occurring in a range between approximately 0.5 Hz to 4 Hz or approximately 30 to 240 beats per minute, are captured by the accelerometer. After taking the envelope of the filtered signal, a bandpass filter, filtering the frequency range of the heart rate, is applied for generating a signal for the heart rate calculation. It should be noted that the definition of the time period in step 2 can also be done for the pulse signal and the respiration signal separately.

In step 14 of FIG. 5 the pulse signal segment within time period defined in step 2 is classified based on the set of predefined parameter values that were extracted in step 13 in a similar way as is done for the respiration signal in step 3 but optimized and adapted for the heart beat, or pulse, signal. In step 15 of FIG. 5 it is decided if the pulse signal segment within the current time period is good or bad, i.e. to be accepted or to be rejected, based on the results of the classification in previous step 14 in a similar way as is done for the respiration signal in step 5, but now adapted for the characteristics of the pulse signal. If the pulse signal segment within the current time period is accepted in step 15, then in step 16 the pulse rate is calculated for the part of the signal that is within the current time period, and, in a similar way the respiration rate is calculated in step 6. Because, the pulse signal segment is classified as good and thus resembles a typical heart beat signal, the value of the pulse rate calculated for this signal segment will be a reliable value. The calculated respiration rate and pulse rate can both be shown on a display (not shown). On the other hand, if the pulse signal segment within the current time period is rejected in step 15, then no pulse rate will be calculated for the pulse signal segment within this time period. In this case the pulse signal within the current time period does not resemble a heart beat signal, and a calculation of the pulse rate for this pulse signal segment will result in an inaccurate value of the pulse rate. Similarly, in step 5 the respiration rate will not be calculated in case the signal segment within the current time period does not resemble a respiration signal. It is also possible that within the same time period the heart beat signal is accepted and the respiration signal is rejected, or vice versa. After step 16 in a step 17 a pulse rate confidence index of the calculated pulse rate is calculated for the part of the pulse signal in the present time period if this pulse signal segment is classified as acceptable, in a similar way a respiration rate confidence index is calculated in step 6 for the respiration signal segment. The pulse rate confidence index indicates the confidence or the accuracy of the pulse rate calculated in step 16. The pulse rate confidence index may be defined using the values of the parameters extracted in step 14 for the corresponding pulse signal segment in combination with the calculated value of the pulse rate. The pulse rate and respiration rate confidence indices provide useful input in further processing of the respiration rate or pulse rate data, for example in proper report of the respiration and/or pulse rate and appropriate respiration and/or pulse rate trend analysis.

Figure 6:
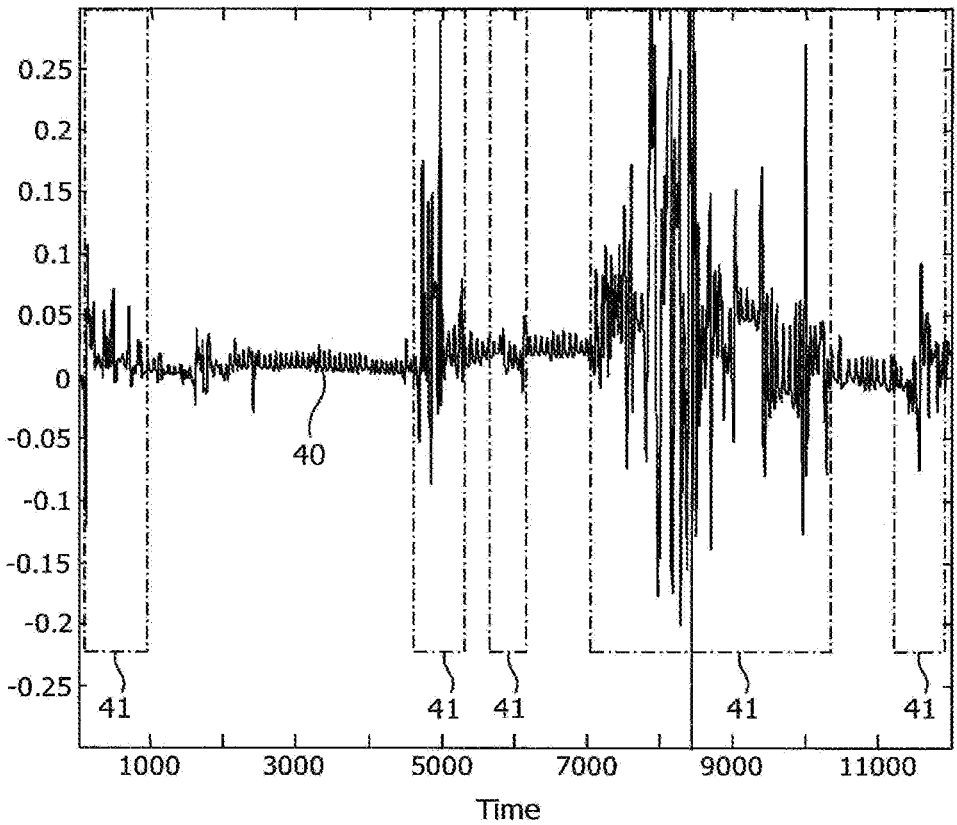
FIG. 6 shows schematically and exemplarily an example of a classification of a cyclic physiological signal.

FIG. 6 shows schematically and exemplarily an example of a classification of a respiration signal 40 applying a method according to the invention. The horizontal axis of the graph in FIG. 6 represents time in arbitrary units and the vertical axis represents the amplitude of the respiration signal 40 in arbitrary units. Shaded or colored bars indicate signal segments 41 that are classified and/or labeled as bad or reject. The respiration signal 40 that is not within the signal segments 41 are classified as good or acceptable signal segments. From FIG. 6 it is clear that the rejected signal segments 41 are contaminated by, for example, motion artifacts and that the signal segments that are not rejected better reflect a breathing signal than the rejected signal segments 41.

Figures 7, 8:
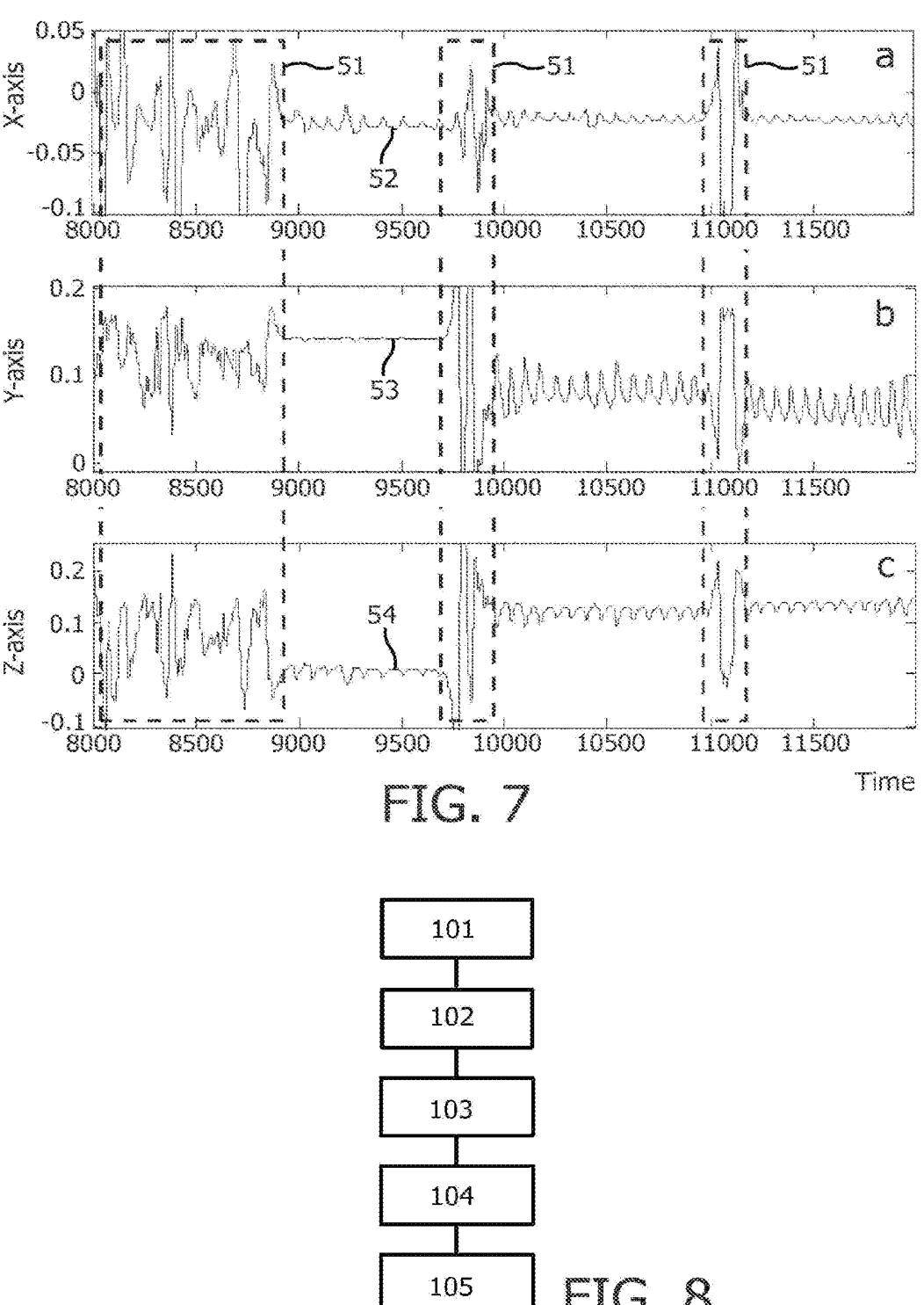
FIG. 7 shows schematically and exemplarily another example of a classification of a cyclic physiological signal measured by a tri-axial accelerometer.
FIG. 8 shows schematically and exemplarily an embodiment of an apparatus adapted for processing a cyclic physiological signal.

FIG. 7 shows schematically and exemplarily another example of a classification of respiration signals 52, 53, 54 measured by a tri-axial accelerometer. FIG. 7 shows three graphs, each reflecting the respiration signal captured for the corresponding spatial axis of the tri-axial accelerometer. The horizontal axis of each graph in FIG. 7 represents time in arbitrary units and the vertical axis represents the amplitude of the x-axis accelerometer respiration signal 52 captured for the spatial x-axis in FIG. 7a, of the y-axis accelerometer respiration signal 53 captured for the spatial y-axis in FIG. 7b and of the z-axis accelerometer respiration signal 54 captured for the spatial z-axis in FIG. 7c. The signal analysis can be performed in parallel for each of the signals 52, 53, 54, wherein in the classification step a comparison between the three different classification results can be done to provide a combined classification of the current time period. Alternatively, the classification is performed on one signal which is a combination of the three signals 52, 53, 54. Shaded or colored bars indicate signal segments 51 that are classified and/or labeled as rejected and from which it is clear that the rejected signal segments 51 are contaminated by, for example, motion artifacts and that the signal segments that are not rejected better reflect a breathing signal than the rejected signal segments 51.

The method according to the invention may be executed by a computer program adapted to carry out the steps as defined in the method according to the invention.

FIG. 8 shows schematically and exemplarily an embodiment of an apparatus adapted for processing a cyclic physiological signal. A sensor 101 captures a cyclic physiological signal from an object, for example a patient. The captured physiological signal is input for a time period definition unit 102 in which a time period is defined for which time period the signal data are collected. The time period definition unit 102 is adapted to repeatedly define a consecutive time period in which a next time period is adjacent to or overlaps with a previous time period. The part of the signal contained in the time period is input for an extraction unit 103, which extracts a set of predefined parameter values from the signal segment in the current time period which has been collected and defined in the time period definition unit 102. The parameters and their values define characteristics that are specific for the physiological signal and the values of the parameters that are extracted for the current signal segment thus characterize the physiological signal segment within the current time period. The extracted parameter values are input for a classification unit 104, which classifies the signal within the current time period based upon the extracted parameter values. In this embodiment, the classified signal is input for a frequency calculation unit 105, which calculates the frequency of the classified cyclic physiological signal based upon the classification results and, optionally, also based on the extracted parameter values.

The monitoring apparatus preferably comprises one or more multi-axial accelerometers, in particular, two tri-axial accelerometers, for being positioned at the person at complementary positions, preferentially at the chest and/or abdomen of a person, in order to monitor respiration and/or heart rate, in particular, under ambulatory conditions. The multi-axial accelerometer is used as an inclinometer to reflect the movement of the object, in particular, to reflect the movement of the abdomen or the chest caused by respiration and/or heart activity. The movement is reflected by an inclination change of a surface of the object, on which the multi-axial accelerometer is positioned. The several spatial axes of the multi-axial accelerometer, which are preferentially three orthogonal axes, record the accelerometer signals equal to the projection of the gravity vector on each of these axes. Preferably, the extraction unit and the classification unit are adapted to analyze the signals of the one or more multi-axial accelerometers in parallel.

The monitoring apparatus and the signal analysis method according to the invention can be used for patient monitoring, in particular, to aid in detecting the acutely ill patients outside the intensive care areas.

Although in the above described embodiments the multi-axial accelerometer has preferentially three orthogonal axes, the multi-axial accelerometer can also have two orthogonal axes or more than three axes. Furthermore, the spatial axis can also include another angle, i.e. in another embodiment the axes can be non-orthogonal.

Although in the above described embodiments, one or two multi-axial accelerometers are used, also more than two accelerometers can be used for determining a breathing rate and/or a heart rate.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A method of processing a cyclic physiological signal, the method comprising the steps of:

repeatedly collecting the cyclic physiological signal using a sensor comprising an accelerometer located on a movable person, the cyclic physiological signal collected over a time period covering two or more cycles of the cyclic physiological signal, a next time period overlaps with a previous time period, wherein each added time period comprises overlapping and non-overlapping segments;

extracting values of a set of predefined parameters from the cyclic physiological signal within each time period, wherein the set of predefined parameters characterize the cyclic physiological signal within the time period as a function of time, frequency, and position in space, wherein the values of the predefined parameters are extracted for the cyclic physiological signal for an entirety of the previous time period and an entirety of the next time period that overlaps with the previous time period;

classifying the non-overlapping segments of each time period of the cyclic physiological signal based upon the extracted values of the set of predefined parameters;

determining an extent to which each time period of the cyclic physiological signal is contaminated by motion artifacts based on the classification of the non-overlapping segments of each time period;

calculating a frequency for each time period of the cyclic physiological signal that is not contaminated by motion artifacts to an extent that is greater than a threshold value and ignoring, during the calculating step, each time period of the cyclic physiological signal that is contaminated by motion artifacts to an extent that is greater than the threshold value;

wherein the predefined parameters characterizing the cyclic physiological signal within the time period as a function of time is one or more of signal variance, peak-to-peak value, signal mean, and temporal correlation;

wherein the predefined parameters characterizing the cyclic physiological signal within the time period as a function of frequency is one or more of dominant frequency and spectral entropy; and wherein the predefined parameters characterizing the cyclic physiological signal within the time period as a function of position in space is correlation between spatial axes.

2. The method of claim 1, further comprising extracting a frequency of the classified physiological signal for each time period.

3. The method of claim 2, wherein the frequency comprises a respiration rate or a heart rate.

4. The method of claim 2, further comprising reporting the extracted frequency.

5. The method of claim 2, further comprising calculating a confidence value for the extracted frequency of the physiological signal within each time period, based upon: (i) the values of the set of predefined parameters extracted from the physiological signal in the corresponding time period; and (ii) the extracted frequency value.

6. The method of claim 5, further comprising reporting the calculated confidence value for the extracted frequency of the physiological signal within each time period.

7. The method of claim 1, wherein classifying comprises labeling each time period as accept or as reject.

8. The method of claim 7, wherein a frequency of the physiological signal is not extracted for each time period that is labeled as reject.

9. The method of claim 1, wherein the physiological signal represents a respiration and/or pulse of a patient.

10. The method of claim 1, wherein classifying is based at least in part upon a statistical database of the set of predefined parameters.

11. The method of claim 1, further comprising conditioning the physiological signal before collecting the physiological signal, wherein the step of repeatedly collecting the physiological signal comprises repeatedly collecting the conditioned signal.

12. The method of claim 11, wherein conditioning the physiological signal before collecting the physiological signal comprising filtering the physiological signal.

13. The method of claim 11, wherein filtering the physiological signal comprises filtering accelerometer signals to collect a breathing signal.

14. The method of claim 11, wherein filtering the physiological signal comprises filtering accelerometer signals to collect a heart signal.

15. The method of claim 1, wherein multiple physiological signals are collected simultaneously and wherein classifying is performed for each of the multiple physiological signals separately.

16. The method of claim 1, wherein the accelerometer comprises a multi-axial accelerometer and wherein the measured physiological signal comprises multiple sub-signals corresponding to the multiple axes and said sub-signals are analyzed synchronously in time.

17. The method of claim 16, wherein repeatedly collecting comprises collecting multiple physiological signals from two tri-axial accelerometers positioned at a chest or abdomen of the movable person.

18. The method of claim 1, wherein repeatedly collecting comprises collecting multiple physiological signals from multiple accelerometers, wherein each of the multiple physiological signals is analyzed separately or in combination.

* * * * *